United States Patent [19]

Mitscher et al.

[11] 4,103,091
[45] Jul. 25, 1978

[54] METHOD FOR THE PREPARATION OF PROSTAGLANDIN INTERMEDIATES FROM A MOLD METABOLITE

[75] Inventors: Lester Allen Mitscher; George Winfred Clark, III, both of Lawrence, Kans.; Gordon Herman Bokelman, Vancouver, Canada

[73] Assignee: The Ohio State University Research Foundation, Columbus, Ohio

[21] Appl. No.: 707,726

[22] Filed: Jul. 22, 1976

Related U.S. Application Data

[63] Continuation-in-part of Ser. No. 611,468, Sep. 8, 1975, abandoned.

[51] Int. Cl.$^2$ .................. C07C 69/38; C07C 69/78

[52] U.S. Cl. .................. 560/106; 260/343.3 P; 260/345.8 P; 260/347.4; 560/193; 560/231

[58] Field of Search .................. 260/476 R, 485 G; 560/106, 193

[56] References Cited

U.S. PATENT DOCUMENTS 3,823,138  7/1974  Van Rheenen .................. 260/485 G Primary Examiner—Jane S. Myers
Attorney, Agent, or Firm—Paul D. Burgauer; Robert L. Niblack

[57] ABSTRACT

This invention provides intermediates which are essential for a new chemical method which converts terrein, a fungal metabolite, to an intermediate which is known to be useful for the preparation of prostaglandins of the C series and analogs of other prostaglandins.

5 Claims, No Drawings

METHOD FOR THE PREPARATION OF PROSTAGLANDIN INTERMEDIATES FROM A MOLD METABOLITE

BACKGROUND OF THE INVENTION

This application is a continuation-in-part of our earlier filed application, U.S. Ser. No. 611,468, filed Sept. 8, 1975, now abandoned.

DETAILED DESCRIPTION OF THE INVENTION

The natural prostaglandins are unsaturated fatty acid derivatives possessing a cyclopentane ring and several oxygen functions and double bonds. They have been detected in most mammalian tissues and are characterized by intense physiological activity. Among the significant properties which they exhibit and which have actual or potential clinical application are the regulation of fertility, the termination of pregnancy, regulation of blood pressure, inhibition of platelet aggregation, regulation of the bronchial airway diameter, mediation of the inflammatory response, control of gastric secretion, and so on. In actual clinical use at the moment are prostaglandins $E_2$ and $F_{2\alpha}$.

Tissues of higher animals and their excreta are not rich enough in prostaglandins to serve as a significant source for large scale production. The sea whip, *Plexaura homomalla,* is the richest natural source now known but harvesting, processing and chemical transformation of prostaglandins from this source is labor intensive, subject to biological variation and time and seasonal influences. Biosynthesis using mammalian enzymes has been used for the preparation of significant amounts of the prostaglandins, but is inadequate to supply world needs and is no longer a primary method of production. Many totally synethtic methods have been described, many of considerable ingenuity, and some of these are now utilized for the commercial production of prostaglandins. These methods all start with optically inactive starting materials and, because the natural prostaglandins are optically active, an essential step in these methods is the resolution of a key intermediate. This entails the loss of at least 50% of the material as representing the unnatural and undesired (except for specialized purposes) enantiomer. Alternatives use living microorganisms as sources of enantioselective enzymes. The greater efficiency of carbon yield of these processes is partially offset by the added labor required. Other attempted solutions to this problem involve the use of expensive asymmetric reagents.

Essential to our inventive process is the use of a conveniently available fungal metabolite, terrein, which has the correct absolute stereochemistry for conversion to the natural prostaglandins without the necessity of optical resolution at any stage of the process. Furthermore, the chemical structure of terrein is such that useful functional groups are present in the molecule in strategic places for the elaboration of the necessary functional groups and molecular features characteristic of the natural prostaglandins. Additionally, the molecule contains sufficient novel features so that the process may be modified at various steps in the synthesis to produce useful artificial analogs of the prostaglandins.

According to one aspect of the invention, terrein is converted to cyclopentenes of the formula

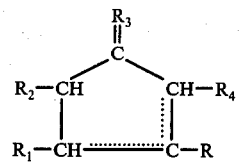

wherein R is —CH=CHCHO, —CHOH—CHOH—CH$_3$, —CH=CHCH$_3$, or —CH=CH—CR$_5$(CH$_2$)$_4$CH$_3$ with R$_5$ being =O or

R$_1$ is part of the double bond of said cyclopentene or R$_6$; R$_2$ is the same R$_6$ as in R$_1$; R$_3$ is =O,

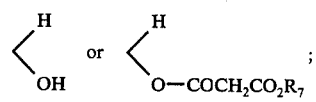

R$_4$ is hydrogen, part of the double bond or forms, together with R$_3$, a γ-lactone of the formula —CH$_2$—CO—O—; R$_6$ is a protective ester group that can be removed chemically without adverse effect on the other substituents of said cyclopentene; and R$_7$ is a loweralkyl moiety.

In essence, the above cyclopentenes are all derived from terrein, which is essential in the preparation of the γ-lactone of formula

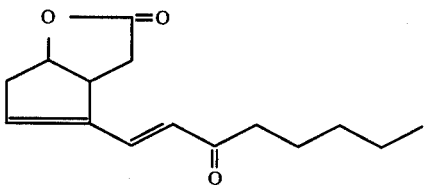

This is a known compound which has been used for making the bioactive prostaglandin C$_2$ as described by Kelly et al. in *Prostaglandins,* Volume 4, page 653 ff. (1973).

The new intermediates which are part of the above formula for cyclopentenes are best identified by reference to the following flow diagrams which show the sequence in which they are made and used. The flow diagrams both start with the known compound terrein and lead to the compound of Structure II shown above.

Conceptually, conversion of terrein to, for example, prostaglandin E$_2$ requires four essential steps arranged in a suitable sequence: (1) the introduction of the C$_7$ side chain with loss of the double bond in the cyclopentenone ring; (2) the introduction of an appropriate oxygen atom, (3) the addition of a 5-carbon aliphatic chain to complete the lower C$_8$ side chain, and (4) the removal of the "extra" hydroxyl group.

More specifically, the current invention is exemplified by the following preferred routes for the conversion of terrein to the known prostaglandin C$_2$ intermediate II:

It will be understood by those skilled in the art that in the case where R$_5$ in side chain R includes the hydroxy group, any number of protective groups may be used to temporarily replace the hydrogen in said -OH. The following diagrams exemplify this with the tetrahydropyranyl group, although t-butoxy or tetrahydrofuranyl and other protective groups that can be removed by treatment with mild acids are equally suitable.
DIAGRAM I
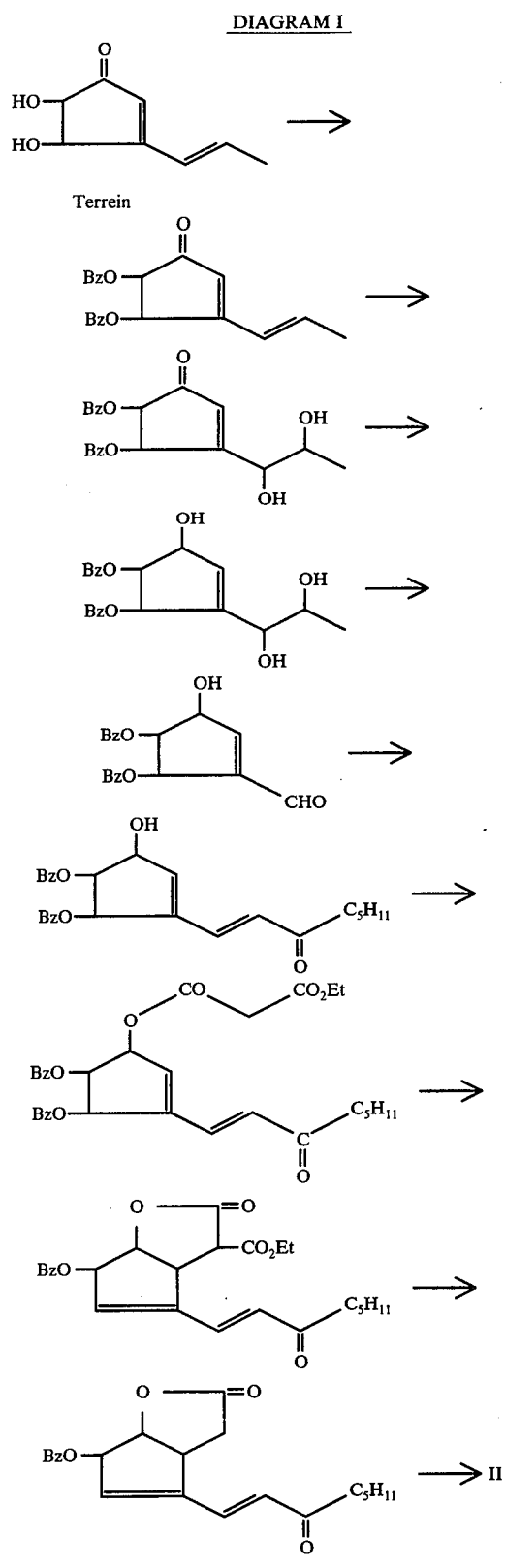
DIAGRAM II
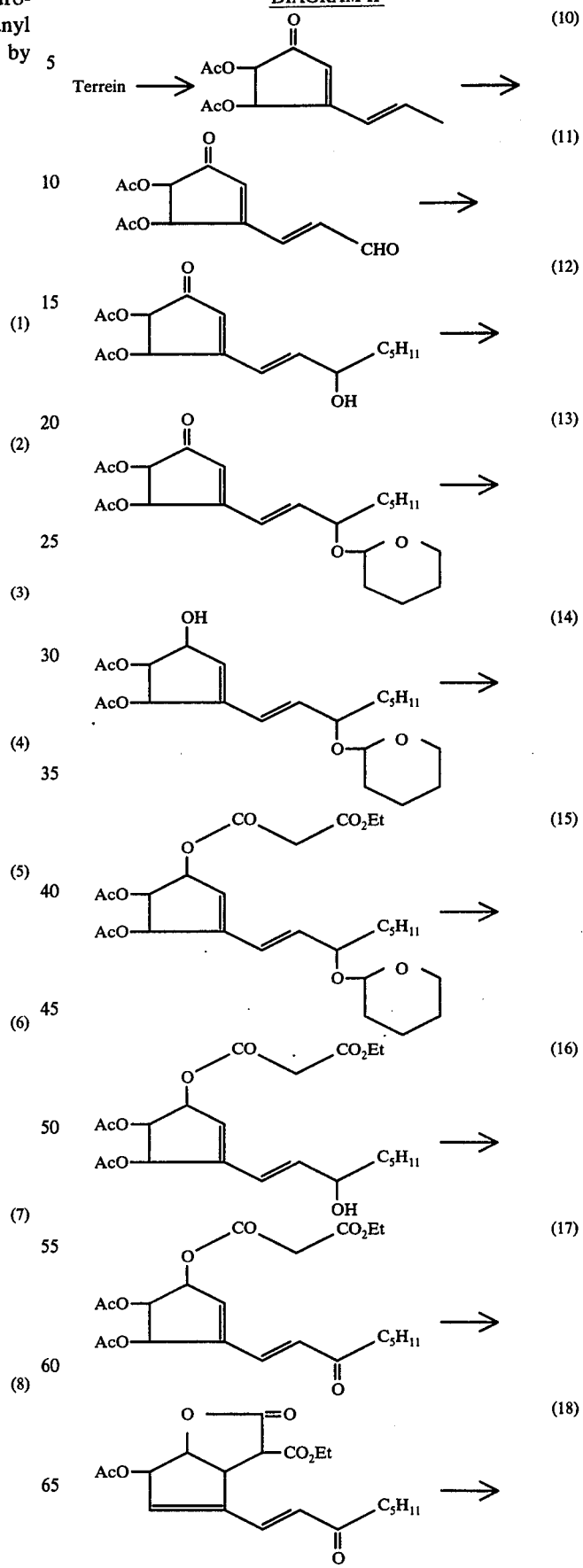

-continued
DIAGRAM II

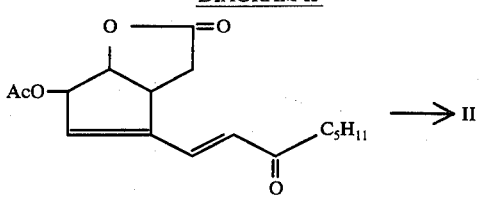
(19)

→ II

In a general embodiment, terrein conveniently obtained in quantity and in a very pure state, as reported in the literature by fermentation of *Aspergillus terreus* [Misawa et al., *Nippon Nogeikagaku Kaishi*, 36,699 (1962)], is converted to its dibenzoyl ester using one of the well known standard means of esterifying an alcohol. For instance, terrein is dissolved in an inert solvent, such as dry tetrahydrofuran, and contacted with an organic acid anhydride and sodium acylate, or with an acid chloride and sodium acylate or, less advantageously, with the acyl anhydride or acyl chloride and an amine such as triethylamine or pyridine, or by using the free acid and dicyclohexylcarbodiimide and the like. The reaction takes place at a temperature between room temperature and the boiling point of the solvent, with some heating preferred in order to minimize formation of the mono ester and to speed the rate of reaction. Obviously, a wide variety of mono- and diesters resulting from the use of a variety of acids may be prepared by simple manipulation of reaction conditions in the manner chemists usually employ.

In the case of $R_6$ being benzoyloxy, the dibenzoate (1) is converted to a glycol (2) using, preferably, osmium tetroxide-barium chlorate mixtures in a reaction inert solvent such as aqueous dioxane. Chemists skilled in the art will recognize that alternate means of preparing such glycols may be employed such as, for example, the use of osmium tetroxide in equivalent quantities, the use of osmium tetroxide in catalytic quantities, as above, but with periodate instead of chlorate, the use of alkaline hydrogen peroxide, the use of hydrogen peroxide in the presence of ferrous sulfate (Fenton's reagent) or of tungstic acid, or the use of iodine and silver benzoate (Prevost's reagent), or the use of iodine and silver acetate in wet acetic acid, and the like. For purposes of characterization, the glycol grouping can be protected and derivatized as the acetonide or a variety of esters. The keto function of glycol (2) is then reduced to the alcohol (3) using known reducing agents of which zinc borohydride and 1-selectride work efficiently. THF is a good solvent for the reduction, but, of course, a wide variety of other solvents and other reducing agents can be employed including the family of alkali metal borohydrides, hydrogen gas with a catalyst, aluminohydrides and so on. The glycol grouping is cleaved to produce the aldehyde (4) by oxidation with sodium periodate in a reaction inert solvent such as aqueous dioxane or THF. Alternately, lead tetraacetate can be employed.

The periodate reaction is facilitated by the use of biphasic solvent mixtures of which water and ether is effective. The lower ($C_8$) side chain of the prostaglandins is then introduced by the use of a Wittig reagent such as the sodium salt of dimethyl-2-oxoheptylphosphonate in a dry solvent, such as THF. Unsaturated ketone (5) is then esterified with an acid chloride or anhydride with an activated methylene or methine group such as acetoacetic acid and its alkylated analogs or a malonyl semiester or one of its alkylated analogs. Preferably for the route illustrated, ethyl malonyl chloride is used. Ester (6) can also be prepared by esterifying alcohol (4) first and then performing the Wittig reaction. The resulting ester (6) is then cyclized using a suitable base, such as sodium hydride, potassium t-butoxide, and the like. Non-nucleophilic bases of sufficient base character to ionize the active methylene or methine of the intermediate ester group are preferred and a variety will suggest themselves to those skilled in the art. These include triethylamine, pyridine, 1,5-diazabicyclo [4.3.0] non-5-ene, etc. Nucleophilic bases may be employed, but the yield often suffers due to partial loss of one or more of the desired ester groups of compound (6). Under the conditions used herein, one of the benzoyl groups is lost during the cyclization process to form intermediate (7) which is advantageously substituted for conversion to the prostaglandin C series. Compound (7) is then converted to intermediate (8) by heating in aqueous glycerine or by hydrolysis using lithium iodide in DMF solvent with or without sodium cyanide added, or through the use of copper acetate in hexamethylphosphortriamide, and the like. The remaining benzoyloxy group of (8) may be removed by a variety of reductive processes of which zinc in acetic acid is one of the most highly effective. Alternate methods for performing this step include the use of, for example, zinc or zinc amalgam in acetic anhydride, aqueous mineral acids, chromium II salts, or calcium in liquid ammonia. Care must be exercised in these reactions to avoid reduction of the double bond of the pentene ring. Many transpositions of the order of the steps in this sequence will suggest themselves to those skilled in the art. These do not lie outside the scope of this invention. An example of such is reaction of ethylmalonyl chloride with the free alcoholic group of aldehyde (4) followed by base catalyzed cyclization in the manner described for the conversion of (6) to (7). Wittig reaction to introduce the lower side chain in the manner exemplified for the conversion of (4) to (5) will then produce (7) which may be converted to II as before.

In another embodiment of the present invention, terrein is converted to Compound II via other intermediates. In this method, terrein is converted to its diacetyl derivative (10) by acetylation under one of the many known esterification conditions of which treatment with acetic anhydride and sodium acetate is the simplest. Diacetylterrrein is then oxidized with selenium dioxide to give conjugated ketoaldehyde (11). The oxidation is most effectively carried out by using freshly sublimed selenium dioxide in an inert atmosphere. The aldehyde function of compound (11) reacts preferentially with organometallic reagents such as amyl Grignard and the like to form the lower ($C_8$) side chain of the prostaglandins. The alcoholic function of (12) is conveniently protected by the use of a variety of ethers capable of subsequent convenient removal with dilute acid of which the tetrahydropyranyl ether has been useful. Temporary protection is required to retain the oxygen function in its designated position. Obviously, those skilled in the art will see that one may also use silyl ethers or other ketals, especially those without anomeric or optically active center such as those prepared from 2,2-dimethoxy-propane or from gamma-pyrone derivatives and the like, in the place of the tetrahydropyranyl ether group. Reduction of the keto function of ether (13) proceeds smoothly under a variety of conditions of which the use of 1-selectride and zinc borohydride are particularly convenient. The newly introduced alcohol function of (14) is then esterified in the usual way with an ester containing an active methylene or methine function. The resulting derivative (15) can be used without isolation and without rigorous purification. The next step involves the removal of the above protective function with dilute acid mixtures to produce (16). Oxidation of (16) can be performed with a variety of reagents of which the Jones procedure ($CrO_3$/$H_2SO_4$/$Me_2CO$), $MnO_2$, and dicyanodichloroquinone are particularly useful. Compound (17) is then cyclized with base or acid catalysts to produce the acetyl analog of compound (7) which then can be converted by known procedures to prostaglandin $C_2$ and its various analogs in a manner analogous to that used in the first process.

Any substitution on the side chains may be made by the known chemistry of the prostaglandins. This will include a variety of aliphatic, aromatic, mixed aromatic aliphatic, branched chain or straight chain and/or side chain substitutions of oxygen and sulfur for methylene, halo substitutions, and such other substitutions as are well known to prostaglandin chemists.

The following examples will serve to illustrate this invention without limiting it thereto.

EXAMPLE 1

PREPARATION OF TERREIN DIBENZOATE (1)

Terrein (18.5g, 0.120 moles) was dissolved in molten benzoic anhydride (265g, 1.17 moles) containing 21g (0.178 moles) of sodium benzoate. The temperature of the melt was maintained at 55°–65°, as higher temperatures induced decomposition. After 7 hours, the reaction was cooled to room temperature, covered with ether and extracted with cold water. Crushed ice was added to the ether layer and the extraction was continued with ice cold 50% (1:1) aqueous ammonium hydroxide. The extraction was continued until no benzoic anhydride was detected by tlc (silica gel G with $CHCl_3$--visualization with iodine vapor). The ether layer was then washed with saturated NaCl solution until the washes were neutral to hydrion paper, dried over $MgSO_4$, filtered and evaporated. Column chromatography on silica gel with chloroform afforded 36.0g (84%) of terrein dibenzoate (1) and 3.98g of 1-, or 2-benzoylterrein. Terrein dibenzoate showed IR bands at 1745 and 1660 cm$^{-1}$; $UV\lambda_{Max}^{EtOH}$ 274 nm (log $\epsilon$ 4.37), 232 nm (log $\epsilon$ 4.47); pmr ($CDCl_3$) 1.88 (d), 5.60 (d), 6.35 (m), 6.45 (s), 6.52 (d), 6.57 (m).

EXAMPLE 2

2$\beta$, 3$\alpha$-Dibenzoyloxy-4-(1,2-dihydroxypropyl)-cyclopent-4-ene-1-one (2)

Terrein Dibenzoate (1) (21.6g, 0.0596 moles) was dissolved at room temperature in 600 ml of dimethylformamide containing 50 ml of water. To this solution was added 1.5g (0.0059 moles) of osmium tetroxide in 20 ml of DMF (9.9 mole%). The solution turned a dark brown-black. After 5 minutes of stirring with nitrogen gas passing through the reaction, 9.60g (0.0298 moles) of barium chlorate dihydrate in 180 ml of water was added slowly over a 3-4 hour period. Before the last few ml of solution had been added, an aliquot of the reaction mixture was quenched in ether/water and showed no starting material present by tlc (silica gel G; chf; permanganate spray). The reaction was poured into three liters of water and extracted with three 500-ml portions of ether. The ether layers were combined, back extracted with four 1-liter portions of water saturated with salt, and then dried over sodium sulfate for one hour. The dried ether layer (still containing the sodium sulfate) was saturated with $H_2S$ gas for 10 minutes and then stirred for 30-40 minutes. The solution was then filtered through celite, evaporated, and vacuum dried for 14 hours to produce a foamy resinous solid which weighed 17.0g (72%) and was essentially pure (2) by tlc (ether): IR bands at 3400–3600 and 1745 cm$^{-1}$; $UV\lambda_{Max}^{EtOH}$ 232nm (log $\epsilon$ 4.64); pmr ($CDCl_3$) 1.22 (d), 3.37 (s), 4.17 (m), 5.5 (m), 6.5 (m), 7.45 and 8.07 (m) $\delta$.

EXAMPLE 3

1$\alpha$-Hydroxy-2$\beta$,3$\alpha$-dibenzoyloxy-4-(1,2-dihydroxypropyl)-cyclopent-4-ene (3)

Diol (2) (6.0g, 0.015 moles) was dissolved in 100 ml THF and added to a solution of zinc borohydride in ether so as to have a 5 mole excess. Under these conditions, a bright yellow color developed which faded slightly with time and a white precipitate formed within 20 minutes. If the precipitate was not redissolved, considerable starting material was recovered. The precipitate was dissolved by the addition of more THF and the solution was stirred until an aliquot showed no more starting material by tlc (ether) when worked up with ether-10% aqueous HCl. The reaction was then cooled in an ice bath and carefully treated with 10HCl aqueous HcL to pH 1. Saturated salt solution (1 liter) was added and the reaction extracted with ether (4 times 150-ml portions). The extracts were combined, dried over sodium sulfate, evaporated, and chromatographed over silica gel with 0.5% EtOH in ether or 2% MeOH in chf to give the desired triol (3) (4.75g, 79% yield): IR bands 3150–3650, 1740 cm$^{-1}$; $UV\lambda_{Max}^{EtOH}$ 232 nm (log $\epsilon$ 4.32); pmr ($CDCl_3$) 1.20 (m), 3.57 (m), 4.00 (m), 4.77 (s), 5.32 (t), 6.10 (m), 6.32 (d), 7.42 (m) and 8.05 (m) $\delta$.

EXAMPLE 4

1,2-Dibenzoyloxy-3-adloxo-cyclopent-3-ene-5-ol (4)

Triol (3) was oxidized with 1 molar equivalent of sodium periodate (3.2g, 0.015 moles) using a biphasic system consisting of 1 part water and 5 parts ether. When tlc examination showed starting material to be absent, the reaction was diluted with water, saturated with sodium chloride, and extracted several times with ether. The ether layers were combined, dried over sodium sulfate, filtered and evaporated. Vacuum drying produced a resinous solid hydroxy-aldehyde (4), 5.1g (96%): IR bands 3150–3650, 1745 and 1710 cm$^{-1}$; $UV\lambda_{Max}^{EtOH}$ 230 nm (log $\epsilon$ 4.43); pmr ($CDCl_3$) 4.18 (m), 4.95 (m), 5.35 (t), 6.60 (d), 7.00 (m), 7.50 (m), 8.03 (m) and 9.92 (s) $\delta$; CIMS, MH$^+$353.

EXAMPLE 5

4(S),5(S)-Dibenzoyloxy-3(R)-hydroxy-1-(3-oxo-trans-1-octenyl)-cyclopentene (5)

A 2-neck 50-ml round bottom flask (containing a magnetic stirring bar) was heated in an oven at 120°, purged with argon and then maintained under a positive pressure of argon. After it had cooled to room temperature, a 0.03047 M THF solution of the sodium salt of dimethyl (2-oxoheptyl)-phosphonate (11.2 ml, 0.341 mM, 1.20 equiv.) was injected into the flask. Next a solution of compound 4 (0.100g, 0.284 mM) dissolved in THF (3 ml) was injected into the flask. The resultant mixture was allowed to stir at room temperature for 45 minutes.

The reaction mixture was then diluted with ether and washed with 5% aq. HCl solution and sat. NaCl solution. The combined aqueous phases were extracted with ether. Next the combined ethereal phases were dried (anh. Na$_2$SO$_4$), filtered and concentrated to a pale yellow oil (0.172g). Purification of the crude product by thick-layer chromatography (silica gel G, 1:24 MeOH-CHCl$_3$, 2 developments) afforded compound (5) as a colorless oil (0.087g, 68%): IR bands 3540, 1735, 1690 (sh), 1645, 1620 cm$^{-1}$; pmr (CCl$_4$) 0.91 (t), 1.06–1.70 (br m), 2.37 (t), 3.66 (br s), 4.73 (m), 5.16 (t), 6.27 (d), 6.38 (m), 7.18 (d), 7.25–8.28 (br m) δ; UVλ$_{Max}^{MeOH}$ 231 nm (log ε 4.48), 264 nm (log ε 4.37); CIMS, MH$^+$ 449.

EXAMPLE 6

3(R)-(4(S),5(S)-Dibenzoyloxy-1-[3-oxo-trans-1-octenyl]-cyclopentenyl) ethyl malonate (6)

A solution of compound (5) (0.058g, 0.130 mM) dissolved in tetrahydrofuran (1.5 ml) was transferred to a 15-ml rb flask that contained a magnetic stirring bar. The flask was warmed to 42°. Next 0.19 ml of a 10% (v/v) solution of ethyl malonyl chloride in THF (0.0238g, 0.158 mM, 1.22 equiv.) was injected into the flask. Then 0.22 ml of a 10% (v/v) solution of triethylamine in THF (0.016g, 0.158 mM, 1.22 equiv.) was injected into the flask. The resultant mixture was stirred for 1 hour at 42° before being cooled to room temperature. Ether was then added to the reaction mixture. The mixture was washed with 10% aq. HCl solution and sat. NaCl solution. The combined aqueous phases were extracted with ether. Next the combined ethereal solutions were dried (anh. Na$_2$SO$_4$), filtered and concentrated to a yellow oil. Purification of this oil by thick-layer chromatography (silica gel G, 1:99 MeOH-CHCl$_3$) yielded compound (6) as a pale yellow oil (0.0517g, 71%): IR bands 1735, 1690 (sh), 1645, 1620 cm$^{-1}$; pmr (CCl$_4$) 0.90 (t), 1.05–1.70 (br m), 2.37 (t), 3.34 (s), 4.12 (q), 5.58 (t), 5.80 (m), 6.28 (d), 6.33 (d), 6.41 (d), 7.7. (d), 7.21–8.19(br m) δ; UVλ$_{Max}^{MeOH}$ 232 nm (log ε 4.46), 264 nm (log ε 4.36); CIMS, 441 (MH$^+$-benzoic acid), etc.

EXAMPLE 7

1(R),5(R),8(r)-benzoyloxy-4(R)-carbethoxy-6-(3-oxo-trans-1-octenyl)-3-oxo-2-oxabicyclo [3.3.0] oct-6-ene (7)

A 2-neck 15-ml round bottom flask (containing a magnetic stirring bar) was heated at 120°, purged with argon and then maintained under a positive pressure of argon. After it had cooled to room temperature, a solution of compound (5) (0.057g, 0.102 mM) dissolved in t-butyl alcohol (3 ml) was injected into the flask. Next a 0.04 M solution of sodium t-butoxide in t-butyl alcohol (0.26 ml, 0.0104 mM, 0.10 equiv.) was injected into the flask. The resultant mixture was stirred for 2.5 hours at room temperature. Then the reaction mixture was warmed to 40° and stirred for an additional 3.5 hours. At the end of that stirring period, more of the sodium t-butoxide solution (0.52 ml, 0.0208 mM, 0.20 equiv.) was added to the reaction mixture, which was then stirred at 40° for an additional 24 hours. Finally, one last portion of the sodium t-butoxide solution (0.52 ml, 0.0208 mM, 0.20 equiv.) was added to the flask and the reaction mixture was refluxed for 16 hours. Next the rb flask was allowed to cool to room temperature and the reaction was quenched by the addition of 10% aq. HCl solution (1 ml). The quenched reaction mixture was concentrated to a residue, which was purified by thick-layer chromatography (silica gel G, 1:99 MeOH-CHCl$_3$, 2 developments). Extraction of the major band afforded compound (7) as a pale yellow oil (0.012g, 27%): IR bands 1790, 1735, 1690 (sh), 1640, 1620 cm$^{-1}$; pmr (CCl$_4$) 0.92 (t), 1.09–1.72 (br m), 2.50 (t), 3.37 (d), 4.17 (br d), 4.32 (q), 5.22 (br d), 5.89 (m), 6.20 (d), 6.31 (br s), 7.26 (d), 7.18–8.17 (br m) δ; UVλ$_{Max}^{MeOH}$ 231 nm (log ε 4.24), 262 nm (log ε 4.37); chemical ionization mass spectrum or CIMS (isobutane) 441 (MH$^+$, 52%).

EXAMPLE 8

1(R),5(R),8(R)-Benzoyloxy-6-(3-oxo-trans-1-octenyl)-3-oxo-2-oxabicyclo [3.3.0] oct-6-ene (8)

Compound (7) (100 mg) was suspended in a mixture of heat dried lithium iodide (6 equivalents) and 0.5 ml of anhydrous pyridine and gently refluxed under a blanket of dry nitrogen for 3 hours. The reaction mixture was cooled to room temperature and poured onto crushed ice. The resulting mixture was extracted with chloroform, the chloroform layers were washed with dilute HCl solution, dried and evaporated. The desired (8) was isolated by preparative tlc as an oil showing an IR band at 1770 cm$^{-1}$ (λ-lactone), no ethyl group in the pmr, and a molecular m/e 368.

EXAMPLE 9

1(R),5(R)-6(3-Oxo-trans-1-octenyl)-3-oxo-2-oxabicyclo[3.3.0 oct-6-ene (II)

Compound (8) (50 mg) was dissolved in 3 ml of glacial acetic acid, 50 mg of zinc dust was added, and the mixture was refluxed for 8 hours. After cooling, the mixture was diluted with 10 ml of water and extracted several times with chloroform. The chloroform layers were dried over anhydrous sodium sulfate, filtered and evaporated in the usual way to give 45 mg of an oil from which the desired (9) was obtained by preparative tlc: IR bands 1760 and 1690 cm$^{-1}$; UVλ$_{Max}^{MeOH}$ 275 nm (log ε 4.30); CIMS, MH$^+$ 249.

EXAMPLE 10

Terrein diacetate (10)

Terrein (0.0308g, 0.20 mM) was dissolved in a mixture of acetic anhydride (3 ml) and anhydrous sodium acetate (0.020g, 0.244 mM). The reaction mixture was stirred for 21 hours at room temperature. Then the acetic anhydride was removed by distillation (0.5 mm Hg at 36°). The residue was dissolved in dichloromethane, filtered and concentrated to yield (10) as a viscous, pale yellow oil (0.0475g, 99.8%): IR bands 3020, 2920, 1745, 1725, 1645, 1585, 1435, 1370, 1350, 1235, 1180, 1055, 1035, 965 cm$^{-1}$; pmr (CDCl$_3$) 1.95 (d of d), 2.15 (s), 5.25 (d), 6.08 (d), 6.2–6.4 (m); UVλ$_{Max}^{CHCl_3}$ 274 nm (log ε 4.21).

EXAMPLE 11

Terrein diacetate (10)

Terrein (6.50g, 42.2 mM) was transferred to a 250 ml Erlenmeyer flask that contained acetic anhydride (50 ml) and a magnetic stirring bar. The resultant slurry was stirred at 0°. Then a solution of anhydrous p-toluenesulfonic acid dissolved in acetic anhydride (15 ml) was added to the flask. After 5 minutes the flask was warmed to room temperature and the reaction mixture (which was now a pink solution) was stirred for an additional 2 hours.

The acetic anhydride was then removed by distillation (0.25 mm Hg at 40°), and the residual brown oil was dissolved in ether. The ethereal solution was washed with cold (0°) 0.1 N NaHCO$_3$ solution and distilled water. The solution was subsequently dried (anh. Na$_2$SO$_4$), filtered and concentrated to a pale yellow oil (8.813g, 88%). Examination by tlc (silica gel G, 49:1 CHCl$_3$-MeOH) revealed that the product was not contaminated with either stirring material or monoacetylated product.

EXAMPLE 12

4(S),5(R)-Diacetoxy-3-(trans-1-propenal)-2-cyclopenten-1-one (11)

Terrein diacetate (10) (14.09g, 59.1 mM) was transferred to a 1 liter round flask that contained a magnetic stirring bar. The starting material was dissolved in 500 ml of xylene, and this solution was then refluxed with stirring. Next freshly resublimed selenium dioxide (9.19g, 82.8 mM, 1.40 equiv.) was added in small portions to the reaction mixture, and a Dean-Stark trap (for removal of water) was inserted between the flask and the reflux condenser.

After 4.5 hours a second portion of SeO$_2$ (9.19 g) was added to the flask. Four hours later, refluxing was stopped and the hot reaction mixture was filtered. The red filtrate was concentrated to a black oil (14.140g). Examination by tlc (silica gel G, 1:24 MeOH-CHCl$_3$) revealed that this oil contained at least 6 components. The desired product (11) gave an immediate positive test with 2,4-dinitrophenylhydrazine spray reagent. The crude reaction product was charged to a 250g silica gel column, which was developed rapidly with CHCl$_3$. The fractions which contained aldehyde (11) were combined to yield a red oil (8.05g). This product was further purified by the use of silica gel (250g) column chromatography again (CHCl$_3$ as the eluting solvent) to afford compound (11) as a pale yellow oil (4.41g, 30%).

The desired product (11) was characterized by the following spectral data: IR bands 3020, 2920, 2820, 2720, 1745–1735 (broad), 1688, 1570, 1370, 1230, 1170, 1110, 1035, 970 cm$^{-1}$; pmr (CDCl$_3$) 2.14 (s), 5.21 (d), 6.15 (d), 6.52 (d of d), 6.69 (s), 7.37 (d of d), 9.70 (d of d); UV$\lambda_{Max}^{CHCl_3}$ 274 nm (log $\epsilon$ 4.19), 284 nm (sh, log $\epsilon$ 4.11); CIMS, MH$^+$ 253 (100%) and 193 (54%, MH$^{+- HOAc}$).

EXAMPLE 13

4(S),5(R)-Diacetoxy-3-(3-hydroxy-trans-1-octenyl)-2-cyclopenten-1-one (12)

A 2-neck 50-ml round bottom flask containing a magnetic stirring bar was heated in an oven at 120°, purged with argon and then maintained under a positive pressure of argon. After the flask had cooled to room temperature, a solution of 1-bromopentane (0.889g, 5.89 mM, 1.26 equiv.) dissolved in tetrahydrofuran (3.5ml) was added by injection. Then a strip of magnesium ribbon (0.156g, 6.42 mM, 1.38 equiv.) was transferred to the flask.

since formation of the Grignard reagent proceeded exothermically, the temperature of the flask was moderated using a beaker of water at room temperature. After 30 minutes of stirring, another 3.5-ml. portion of THF was injected to dissolve the white precipitate which had formed. Thirty minutes later, 3.5-ml. of ether was injected into the flask, which was then cooled to −78°.

Next a solution of the starting aldehyde (11) (1.175g, 4.66 mM, 1.0 equiv.) dissolved in a mixture of THF (3.5 ml) and Et$_2$O (3.5 ml) was injected into the flask. The resultant brown slurry began to solidify. Solidification was avoided by the use of vigorous stirring and the injection of more ether (4 ml). The reaction mixture was stirred for an additional 3.5 hours at −78°. The mixture was then poured into a rapidly stirring 10% aq. HCl solution. The ethereal layer was removed and the aqueous layer was extracted with ether. The combined ethereal phases were dried (anh. Na$_2$SO$_4$), filtered and concentrated to a brown oil (1.297g).

The crude reaction product was purified by silica gel (130 g) column chromatography (1:24 MeOH-CHCl$_3$ as the eluting solvent mixture) to yield a mixture of the two epimeric alcohols (12). The purified product was a pale yellow oil (0.779 g, 52%): IR bands 3700–3460 (broad), 2920, 2840, 1745, 1725 (sh), 1638, 1580, 1370, 1095, 980 cm$^{-1}$; pmr (CDCl$_3$) 0.90 (t), 1.10–1.70 (br m), 2.14 (s), 2.15 (s), 2.57 (br s), 4.16–4.40 (m), 5.22 (d), 6.09 (d), 6.20–6.35 (m); UV$\lambda_{Max}^{CHCl_3}$ 272 nm (log $\epsilon$ 4.22).

EXAMPLE 14

4(S),5(R)-Diacetoxy-3-(3-[2-tetrahydropyranyloxy]-trans-1-octenyl)-2-cyclopenten-1-one (13)

Compund (12) (0.050g, 0.154 mM) was transferred as a neat liquid to a 5-ml round bottom flask which contained a magnetic stirring bar. This starting material was dissolved in ether (0.25 ml). Next dihydropyrane (0.02 ml, 0.019 g, 0.232 mM, 1.5 equiv.) was added to the flask. Then a solution of p-toluenesulfonic acid (0.0016g, 0.0092 mM, 0.06 equiv.) dissolved in ether (0.25 ml) was transferred to the reaction flask.

The reaction mixture was stirred for 2 hours at room temperature, during which time the color of the mixture changed from pale yellow to brown. Then sat. NaHCO$_3$ solution and more ether were added to the flask. After the aqueous phase was removed, the ethereal phase was washed with sat. NaHCO$_3$ solution, distilled water and sat. NaCl solution. Next the ethereal phase was dried (anh. Na$_2$SO$_4$), filtered and concentrated to yield a brown oil (65.7 mg). Purification of the crude product by thick layer chromatography (silica gel G, 1:32 MeOH-CHCl$_3$) afforded THP-ether (13) as a pale yellow oil (44.2 mg, 70%): IR bands 3000, 2940, 2860, 1745, 1730 (sh), 1640, 1465, 1450, 1440, 1375, 1240, 1125, 1080, 1025, 970 cm$^{-1}$; pmr (CDCl$_3$) 0.89 (t), 1.10–1.55 (br m), 1.63 (m), 2.13 (s), 2.15 (s), 3.4–4.2 (m), 4.58 (br s), 5.20 (d), 6.09 (d), 6.16–6.20 (m); UV$\lambda_{Max}^{CHCl_3}$ 274 nm (log $\epsilon$ 4.20), 326 nm (sh, log $\epsilon$ 3.23 ).

EXAMPLE 15

4(S),5(S)-Diacetoxy-1-(3-[2-tetrahydropyranyloxy]-trans-1-octenyl)-cyclopenten-3-ol (14)

A 2-neck 15-ml round bottom flask containing a magnetic stirring bar was heated in an oven at 120°, purged with argon and then maintained under a positive pressure of argon. After it had cooled to room temperature, a solution of ketone (13) (0.052g, 0.127 mM) dissolved in tetrahydrofuran (1.1 ml) was injected into the flask. The flask was then cooled to −78°.

Next 0.14 ml of a 1.107 M solution of lithium tri-sec-butylborohydride (obtained from Aldrich under the name of "1-selectride") (0.155 nM, 1.22 equiv.) was injected dropwise into the flask. This addition caused the color of the reaction mixture to change from pale yellow to yellowish brown. After 2 hours of stirring at −78°, a 10% aq. HCl solution (0.1 ml) was injected into the flask. The flask was allowed to warm to room temperature and then more HCl solution (8 drops) was added to adjust the reaction mixture to pH 6. The final acidification caused the color of the reaction mixture to change to pale yellow. After the acidified reaction mixture had stirred at room temperature for an additional 45 minutes, ether and distilled water were added. The aqueous phase was removed and then the ethereal phase was washed with water and sat. NaCl solution. Next the ethereal phase was dried (anh. Na$_2$SO$_4$), filtered and concentrated to a pale yellow oil (69.5 mg). Purification of the crude oil by thick layer chromatography (silica gel G, 1:24 MeOH-CHCl$_3$) yielded the reduced product (14) as a pale yellow oil (37 mg, 71%): IR bands 3640–3300 (broad), 2920, 2855, 1735, 1450, 1370, 1125, 970 cm$^{-1}$; pmr (CDCl$_3$) 0.89 (t), 1.09–1.52 (br m), 1.63 (m), 2.06 (s), 2.09 (s), 2.78–3.05 (br s), 3.3–4.2 (m), 4.57 (br s), 5.15–6.22 (br m) δ; UVλ$_{Max}^{CHCl_3}$ 236 nm (log ε 3.84); CIMS, 393 (MH$^+$-H$_2$O).

EXAMPLE 16

3-(4(S),5(S)-Diacetoxy-1-[3-hyddroxy-trans-1-octenyl]-cycloentenyl) ethyl malonate (16)

Alcohol (14) (0.0285g, 0.0694 mM) was transferred to a 15-ml round bottom flask that contained a magnetic stirring bar. Tetrahydrofuran (0.8 ml) was added to the flask and, after the starting material had dissolved, the flask was cooled to 0° C. Next 0.10 ml of a 10% (v/v) solution of ethyl malonyl chloride (obtained from Aldrich, Lot. No. 112137) in THF (0.0125g, 0.0831 mM, 1.2 equiv.) was injected into the flask. Then 0.10 ml of an 11.6% (v/v) solution of triethylamine in THF (0.0084g, 0.0831 mM, 1.2 equiv.) was injected into the flask. Upon the addition of triethylamine, the pale yellow reaction mixture became cloudy. The reaction mixture was stirred for 2 hours at 0° and was then allowed to warm to room temperature. After the mixture had stirred for an additional 1.5 hours at room temperature, 0.05 N HCl solution (1 ml) was added to the flask. Next conc. HCl reagent (3 drops) was added to adjust the reaction mixture to pH 1. This acidified reaction mixture was stirred for 1 hour.

Ether and distilled water were then added to the reaction mixture. The aqueous layer was removed and the ethereal layer was washed with distilled water, dried (anh. Na$_2$SO$_4$), filtered and concentrated to a yellow oil (0.036 g). Purification of the crude oil by thick layer chromatography (silica gel G, 1:24 MeOH-CHCl$_3$, 2-developments) afforded the desired product (16) as a pale yellow oil (18.6 mg, 61%): IR bands 3600–3420 (broad), 2935, 2870, 1735, 1655, 1460, 1375, 1310, 1125, 980 cm$^{-1}$; pmr (CDCl$_3$) 0.89 (t), 1.06–1.75 (br m), 1.28 (t), 2.07 (br s), 3.37 (br s), 3.58 (br s), 4.19 (q), 4.3–4.5 (m), 5.09–5.21 (m), 5.23–6.25 (br m) δ; UVλ$_{Max}^{CHCl_3}$ 237 nm (log ε 3.87).

EXAMPLE 17

3(R)-(4(S), 5(S)-Diacetoxy-1-[3-oxo-trans-1-octenyl]-cyclopentenyl)ethyl malonate (17)

Compound (16) (50 mg) in 5 ml of dioxane was treated with 40 mg of 2,3-dichloro-5,6-dicyano-1,4-benzoquinone and stirred for 24 hours at 50° under a nitrogen atmosphere. The reaction was cooled and filtered. The solids were washed with methylene chloride, and the washings and the filtrate were evaporated. The desired (17) was purified by preparative tlc: UV λ$_{Max}$$^{EtOH}$ 265 nm (log ε 4.38); a new IR band at 1690 cm$^{-1}$; CIMS, MH$^+$ 439.

EXAMPLE 18

1(R),5(R),8(R)-Acetoxy-4-(R)-carbethoxy-6-(3-oxo-trans-1-octenyl)-3-oxo-2-oxabicyclo[3.3.0]oct-6-ene (18)

Compound (17) (0.050g) was dissolved in t-butyl alcohol and treated with a molar equivalent of potassium t-butoxide in t-butyl alcohol under an argon atmosphere at 40° for 24 hours. The reaction was cooled to room temperature and quenched by the addition of 10% aq. HCl solution (1 ml) and evaporated. Preparative tl-chromatography produced the desired (18) as a pale oil possessing an IR band at 1690 cm$^{-1}$; UVλ$_{Max}^{EtOH}$265 nm; pmr 6.30 δ (br s); CIMS, MH$^+$ 379.

EXAMPLE 19

1(R),5(R),8(R)-Acetoxy-6-(3-oxo-trans-1-octenyl)-3-oxo-2-oxabicyclo[3.3.0]oct-6-ene (19)

Compound (18) (120 mg) was partially dissolved in anhydrous pyridine and 6 equivalents of anhydrous (heat dried in vacuum) lithium iodide was added. After covering the mixture with a blanket of dry nitrogen gas, the mixture was refluxed for 3.5 hours. After cooling and pouring onto crushed ice, the mixture was extracted with chloroform, dried over anhydrous sodium sulfate, filtered and evaporated. Compound (19) is obtained as an oil following preparative tlc. In addition to an IR band at 1770 cm$^{-1}$ indicative of a λ-lactone and the absence of an ethyl absorption in the pmr spectrum, a UV maximum at 265 nm and a protonated molecular ion at MH$^+$ = 307 characterize substance (19).

[Note it is a diastereoisomer of a compound described by P. Crabbe et. al., Tetrahedron Letters 3021 (1973)].

EXAMPLE 20

1(R),5(R)-6(3-oxo-trans-1-octenyl)-3-oxo-2-oxabicyclo[3.3.0]oct-6-ene (II)

Compound (19) (75 mg) is dissolved in 3 ml of glacial acetic acid, 50 mg of zinc dust is added, and the mixture is refluxed for 9 hours. After cooling, the compound (9) is isolated as described in Example 9 and is found to have the same spectroscopic and chromatographic properties as stated previously.

What is claimed is:

1. A cyclopentene of the formula:

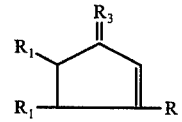

wherein R is —Ch═CHCHO, —CHOH—CHOH—CH$_3$, —CH═CHCH$_3$ or —CH═Ch—CR$_5$(CH$_2$)$_4$CH$_3$ with R$_5$ being ═O or

;

both R$_1$ are benzoyloxy or acetoxy; R$_3$ is

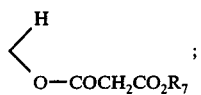
and R₇ is a loweralkyl moiety.
2. The compound of claim 1 wherein R is —CH=CH—CR₅—C₅H₁₁ with R₅ representing =O or
R₁ is benzoyloxy or acetoxy, R₃ is
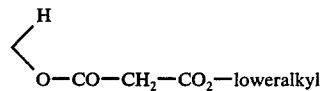
3. The compound of claim 2 wherein said loweralkyl is ethyl and R₅ is oxo.
4. The compound of claim 3 wherein R₁ is benzoyloxy.
5. The compound of claim 3 wherein R₁ is acetoxy.
* * * * *